United States Patent
Yamane et al.

(10) Patent No.: US 12,224,063 B2
(45) Date of Patent: Feb. 11, 2025

(54) INFORMATION PROCESSING DEVICE, INFORMATION PROCESSING METHOD, AND INFORMATION PROCESSING SYSTEM

(71) Applicant: SONY GROUP CORPORATION, Tokyo (JP)

(72) Inventors: Kenji Yamane, Tokyo (JP); Shinji Watanabe, Tokyo (JP); Takeshi Kunihiro, Tokyo (JP); Kazuki Aisaka, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 443 days.

(21) Appl. No.: 17/432,165

(22) PCT Filed: Feb. 18, 2020

(86) PCT No.: PCT/JP2020/006240
§ 371 (c)(1),
(2) Date: Aug. 19, 2021

(87) PCT Pub. No.: WO2020/175238
PCT Pub. Date: Sep. 3, 2020

(65) Prior Publication Data
US 2022/0172840 A1    Jun. 2, 2022

(30) Foreign Application Priority Data
Feb. 28, 2019    (JP) .................. 2019-035744

(51) Int. Cl.
*G16H 50/20* (2018.01)
*G06T 7/00* (2017.01)
*G16H 30/40* (2018.01)

(52) U.S. Cl.
CPC .......... *G16H 50/20* (2018.01); *G06T 7/0014* (2013.01); *G16H 30/40* (2018.01); *G06T 2207/30096* (2013.01)

(58) Field of Classification Search
CPC ...... G16H 50/20; G16H 30/40; G06T 7/0014; G06T 2207/30096; G06T 2207/20081;
(Continued)

(56) References Cited

U.S. PATENT DOCUMENTS

2016/0110584 A1    4/2016 Remiszewski et al.
2017/0323447 A1*   11/2017 Tsukagoshi ............ A61B 6/467
(Continued)

FOREIGN PATENT DOCUMENTS

CN    107835654 A    3/2018
EP    3207499 A1    8/2017
(Continued)

OTHER PUBLICATIONS

International Search Report and Written Opinion of PCT Application No. PCT/JP2020/006240, issued on May 26, 2020, 08 pages of ISRWO.

*Primary Examiner* — Dhaval V Patel
(74) *Attorney, Agent, or Firm* — CHIP LAW GROUP

(57) ABSTRACT

An information processing device is provided that includes an identification data acquisition unit that acquires image data for identification in which a first biological region is captured and first site information of the first biological region, and an identification unit that selects an identifier corresponding to the first site information from identifiers associated respectively with a plurality of pieces of site information, and performs an identification process on the basis of the identifier and the image data for identification.

19 Claims, 12 Drawing Sheets

(58) Field of Classification Search
CPC .... G06T 2207/30024; G06T 2207/30204; G01N 33/48
See application file for complete search history.

(56) References Cited

U.S. PATENT DOCUMENTS

| | | |
|---|---|---|
| 2018/0070798 A1 | 3/2018 | Kamiyama et al. |
| 2018/0336395 A1 | 11/2018 | Madabhushi et al. |
| 2019/0139646 A1* | 5/2019 | Roberts .................. G16H 50/30 |
| 2019/0209116 A1* | 7/2019 | Sjöstrand ............... G16H 50/30 |
| 2019/0266486 A1* | 8/2019 | Yamada .................... G06N 3/08 |
| 2020/0005472 A1 | 1/2020 | Terunuma et al. |

FOREIGN PATENT DOCUMENTS

| | | |
|---|---|---|
| EP | 3590577 A1 | 1/2020 |
| JP | 2015-116319 A | 6/2015 |
| JP | 2018-502275 A | 1/2018 |
| JP | 2018-185265 A | 11/2018 |
| KR | 10-2017-0118032 A | 10/2017 |
| WO | 2016/061586 A1 | 4/2016 |
| WO | 2016/185617 A1 | 11/2016 |
| WO | 2018/159775 A1 | 9/2018 |

* cited by examiner

| SITE INFORMATION | SCAN DATA STORAGE LOCATION | LEARNER INFORMATION | MODEL INFORMATION | IDENTIFIER INFORMATION |
|---|---|---|---|---|
| STOMACH | /home/gastro | Gust_1 | G1 | GG1 |
| LARGE INTESTINE | /home/colon | Colon_1 | C1 | CC1 |
| LIVER | /home/liver | Liver_1 | L1 | LL1 |

| SITE INFORMATION | ANALYSIS SERVER |
|---|---|
| STOMACH | ANALYSIS SERVER 1 |
| LARGE INTESTINE | ANALYSIS SERVER 2 |
| LIVER | ANALYSIS SERVER N |

141

INFORMATION PROCESSING DEVICE, INFORMATION PROCESSING METHOD, AND INFORMATION PROCESSING SYSTEM

CROSS REFERENCE TO RELATED APPLICATIONS

This application is a U.S. National Phase of International Patent Application No. PCT/JP2020/006240 filed on Feb. 18, 2020, which claims priority benefit of Japanese Patent Application No. JP 2019-035744 filed in the Japan Patent Office on Feb. 28, 2019. Each of the above-referenced applications is hereby incorporated herein by reference in its entirety.

TECHNICAL FIELD

The present disclosure relates to an information processing device, an information processing method, and an information processing system.

BACKGROUND ART

In recent years, there has been known a technique for performing an identification process on the basis of image data for identification in which a biological region is captured and an identifier. For example, the identification process can be diagnostic information indicating whether or not there is a lesion in the biological region. Here, a technique for performing an identification process on the basis of image data and an identifier has been disclosed (see, for example, Patent Document 1). In such a technique, data (model data) used by the identifier is generated on the basis of image data for learning.

CITATION LIST

Patent Document

Patent Document 1: Japanese Patent Application Laid-Open No. 2015-116319

SUMMARY OF THE INVENTION

Problems to be Solved by the Invention

However, it is desired to provide a technique capable of improving accuracy of an identification process based on image data for identification in which a biological region is captured.

Solutions to Problems

According to the present disclosure, there is provided an information processing device including an identification data acquisition unit that acquires image data for identification in which a first biological region is captured and first site information of the first biological region, and an identification unit that selects an identifier corresponding to the first site information from identifiers associated respectively with a plurality of pieces of site information, and performs an identification process on the basis of the identifier and the image data for identification.

According to the present disclosure, there is provided an information processing method including acquiring, by a processor, image data for identification in which a first biological region is captured and first site information of the first biological region, and selecting, by the processor, an identifier corresponding to the first site information from identifiers associated respectively with a plurality of pieces of site information, and performing, by the processor, an identification process on the basis of the identifier and the image data for identification.

According to the present disclosure, there is provided an information processing system including an information processing device, in which the information processing device includes an imaging unit that captures an image of a first biological region, an identification data acquisition unit that acquires image data of the first biological region captured by the imaging unit and first site information of the first biological region, and an identification unit that selects an identifier corresponding to the first site information from identifiers associated respectively with a plurality of pieces of site information, and performs an identification process on the basis of the identifier and the image data.

According to the present disclosure, there is provided an information processing system including a medical image imaging device and software used for processing image data corresponding to an object imaged by the medical image imaging device, in which the software causes an information processing device to execute an identification process based on first image data corresponding to a first biological region and an identifier corresponding to the first site information of the first biological region.

BRIEF DESCRIPTION OF DRAWINGS

FIG. 13 is a diagram illustrating an example of site-specific data stored by a site-specific data holding unit according to modification example 2.

MODE FOR CARRYING OUT THE INVENTION

Figure 1:
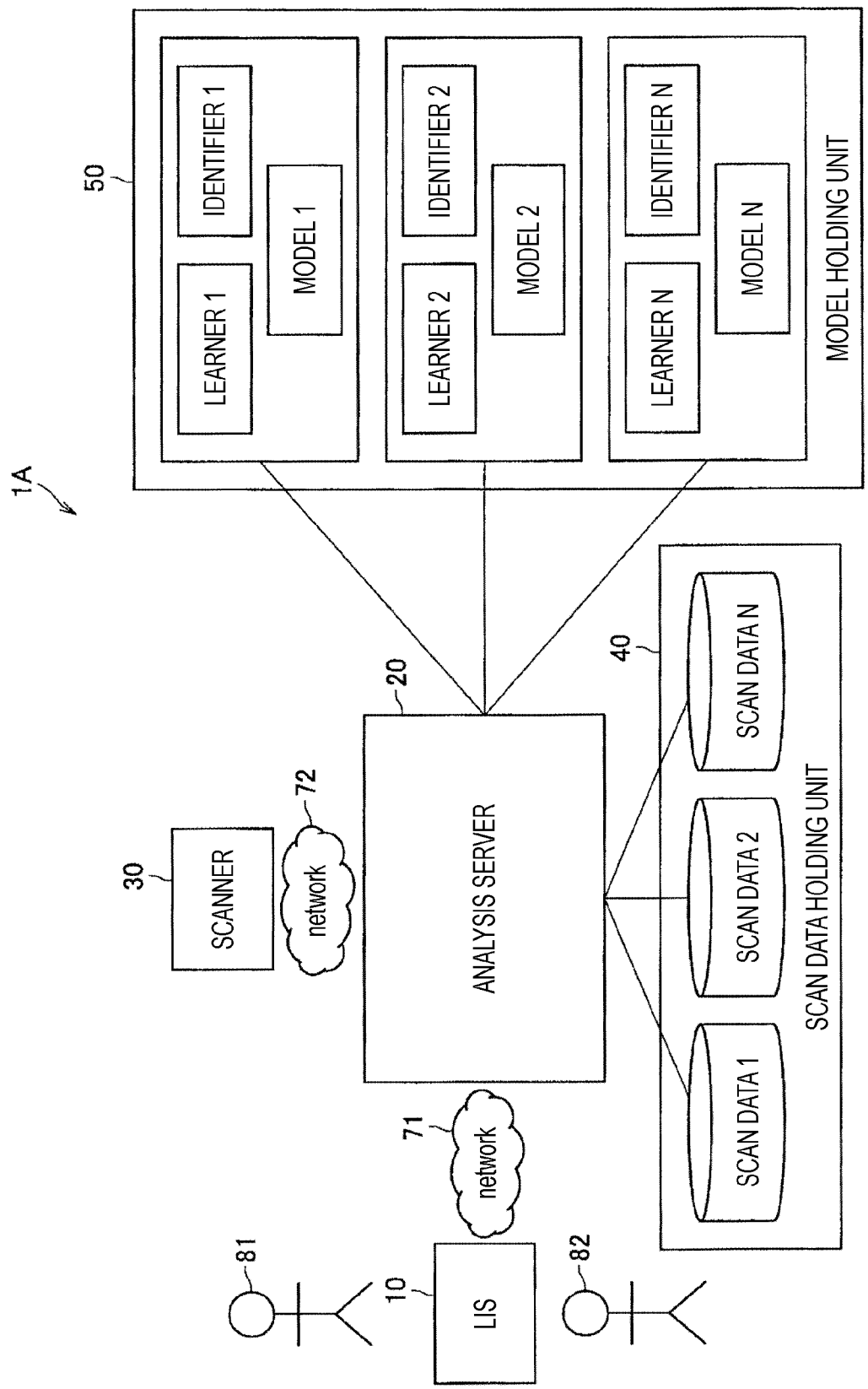
FIG. 1 is a diagram illustrating a configuration example of an information processing system according to an embodiment of the present disclosure.

Hereinafter, preferred embodiments of the present disclosure will be described in detail with reference to the accompanying drawings. Note that in the description and the drawings, components having substantially the same function and configuration are denoted by the same reference numerals, and redundant descriptions are omitted.

Furthermore, in the description and the drawings, a plurality of components having substantially the same or similar functional structures may be distinguished by adding different numerals after the same reference signs. However, in a case where it is not necessary to particularly distinguish each of the plurality of components having substantially the same or similar functional structures, only the same reference numerals are given. Furthermore, similar components of different embodiments may be distinguished by adding different alphabets after the same reference numerals. However, in a case where it is not particularly necessary to distinguish each of the similar components, only the same reference numerals are given.

Note that the description will be made in the following order.

0. Outline
1. Details of embodiment
1.1. Configuration example of information processing system
1.2. Functional configuration example of LIS
1.3. Functional configuration example of analysis server
1.4. Details of functions of system
1.4.1. Sample reception process
1.4.2. Data registration process
1.4.3. Model generation process
1.4.4. Display process
1.4.5. Identification process
2. Modification example
3. Hardware configuration example
4. Conclusion

0. Outline

In recent years, digital pathology is known as a technical methodology for reading a specimen with a scanner to generate a digital image (image data), displaying the generated image data on a display, and allowing a doctor to observe the displayed image data. According to such a digital pathology, it is possible to make a diagnosis by a doctor located in a remote place away from the subject, and it is said that the problem of a shortage of doctors in rural areas can be solved.

Moreover, data used by an identifier (hereinafter, also called "model data") can be generated by performing supervised learning (using deep learning or the like) on the basis of the image data and the correct answer data by using a diagnostic result for the image data as the correct answer data. By using the model data generated in this manner, the identifier can automatically perform the diagnosis on the basis of newly input image data. Accordingly, researches are underway to enable automatic diagnosis with higher accuracy. For example, a competition is held such that image data in which a lesion is captured and the type of the lesion (correct answer) are provided, and it is competed how much the diagnosis can be made according to the correct answer on the basis of the image data.

In order to utilize such automatic diagnosis clinically, even if image data is obtained in which any site of the biological region is captured, it is desired that a diagnosis with respect to the image data is possible. However, under the present circumstances, only researches on generation of model data specialized for one site are conducted. For example, if model data obtained by learning only with respect to image data in which one site is captured is used to make a diagnosis based on image data in which another site is captured, the correct answer rate of the diagnosis does not improve because the configuration is different for every site.

Alternatively, a method of learning on the basis of image data in which each of a plurality of sites is captured is also assumed. Thus, one model data corresponding to a plurality of sites is generated. However, by such a method, it is expected that a huge amount of time is required for learning (or hardware resources required for learning will be enormous) because data sets required for learning become enormous compared to cases where the learning is performed using image data in which one site is captured.

Accordingly, an embodiment of the present disclosure mainly proposes a technique capable of improving accuracy of identification process based on image data for identification in which a biological region is captured. More specifically, the embodiment of the present disclosure proposes a technique that can improve the accuracy of identification process based on image data for identification while reducing resources (time or hardware resources) necessary for generating model data used for an identifier.

The outline of the embodiment of the present disclosure has been described above.

1. Details of Embodiment

1.1. Configuration Example of Information Processing System

Hereinafter, a configuration example of an information processing system according to the embodiment of the present disclosure will be described with reference to the drawings. FIG. 1 is a diagram illustrating a configuration example of an information processing system according to the embodiment of the present disclosure. As illustrated in FIG. 1, an information processing system 1A according to the embodiment of the present disclosure has a laboratory information server (LIS) 10 (another information processing device), an analysis server 20 (information processing device), a scanner 30 (reading device), a network 71, a network 72, a scan data holding unit 40, and a model holding unit 50. The LIS 10 and the analysis server 20 are capable of communicating with each other via the network 71. The analysis server 20 and the scanner 30 are capable of communicating with each other via the network 72.

The LIS 10 includes, for example, a computer. For example, the LIS 10 is used by a technician 81 and a doctor 82. In the embodiment of the present disclosure, it is mainly assumed a case where various operations by the technician 81 are directly input to the LIS 10. However, various operations by the technician 81 may be input to the LIS 10 via a terminal that is not illustrated. Furthermore, in the embodiment of the present disclosure, it is mainly assumed a case where various presented information for the technician 81 is directly output from the LIS 10. However, the various presented information for the technician 81 may be output from the LIS 10 via a terminal that is not illustrated.

Similarly, in the embodiment of the present disclosure, it is mainly assumed a case where various operations performed by the doctor 82 are directly input to the LIS 10. However, the various operations by the doctor 82 may be input to the LIS 10 via a terminal that is not illustrated. Furthermore, in the embodiment of the present disclosure, it is mainly assumed a case where various presented information for the doctor 82 is directly output from the LIS 10.

However, the various presented information for the doctor 82 may be output from the LIS 10 via a terminal that is not illustrated.

The scanner 30 reads a biological region. Thus, the scanner 30 generates scan data including image data in which the biological region is captured. As will be described later, the biological region can correspond to a specimen obtained from a sample. For example, the scanner 30 has an image sensor and captures an image of a specimen with the image sensor, to thereby generate scan data including image data in which the specimen is captured. The reading method of the scanner 30 is not limited to a specific type. For example, the reading method of the scanner 30 may be a charge coupled device (CCD) type or a contact image sensor (CIS) type.

Here, the CCD type can correspond to a type in which reflected light from the specimen is reflected and concentrated on a mirror, light transmitted through a lens is read by the CCD sensor, and the light read by the CCD sensor is converted into image data. On the other hand, the CIS method can correspond to a type in which an RGB three-color light emitting diode (LED) is used as a light source, reads a result of reflection of light from the light source on the specimen with a photosensor, and converts the read result into image data.

The analysis server 20 includes, for example, a computer. For example, the analysis server 20 is connected to the scan data holding unit 40 and the model holding unit 50. Note that in the embodiment of the present disclosure, it is mainly assumed a case where the scan data holding unit 40 and the model holding unit 50 exist outside the analysis server 20. However, at least one of the scan data holding unit 40 or the model holding unit 50 may be incorporated inside the analysis server 20.

The scan data holding unit 40 includes a memory and stores N pieces of scan data (where N is an integer of two or more) generated by the scanner 30.

The model holding unit 50 includes a memory and stores N combinations of a learner, an identifier, and model data (hereinafter, also simply referred to as a "model") (where N is an integer of two or more). Here, the learner and the identifier are provided for every site. Furthermore, the model data is generated by the learner and used by the identifier. Specific examples of the site include a stomach, a large intestine, a liver, and the like, as will be described later. However, the site is not limited to these examples.

For example, information indicating a site (site information) may be information in which the biological region is classified into a clinically meaningful predetermined unit. Then, the clinically meaningful unit may be an organ system, an organ, a tissue, or a disease code. The disease code may be of the International Statistical Classification of Diseases and Related Health Problems (ICD) prepared by the World Health Organization (WHO).

Note that in the embodiment of the present disclosure, it is mainly assumed a case where each of the learner and the identifier is implemented by a neural network. In such cases, the model data may correspond to a weight of each neuron in the neural network. However, each of the learner and the identifier may be implemented by other than the neural network. It may be implemented by a random forest, by a support vector machine, or by AdaBoost.

Furthermore, in the embodiment of the present disclosure, it is mainly assumed a case where the LIS 10, the analysis server 20, and the scanner 30 exist as separate devices. However, a part or all of the LIS 10, the analysis server 20, and the scanner 30 may exist as one device. Alternatively, a part of functions possessed by the LIS 10, the analysis server 20, and the scanner 30 may be incorporated into another device. For example, as will be described in a later modification example, a part of functions of the analysis server 20 (for example, selection of a learner and an identifier based on site information) may be possessed by the LIS 10 instead of the analysis server 20.

The configuration example of the information processing system 1A according to the embodiment of the present disclosure has been described above.

1.2. LIS Functional Configuration Example

Figure 2:
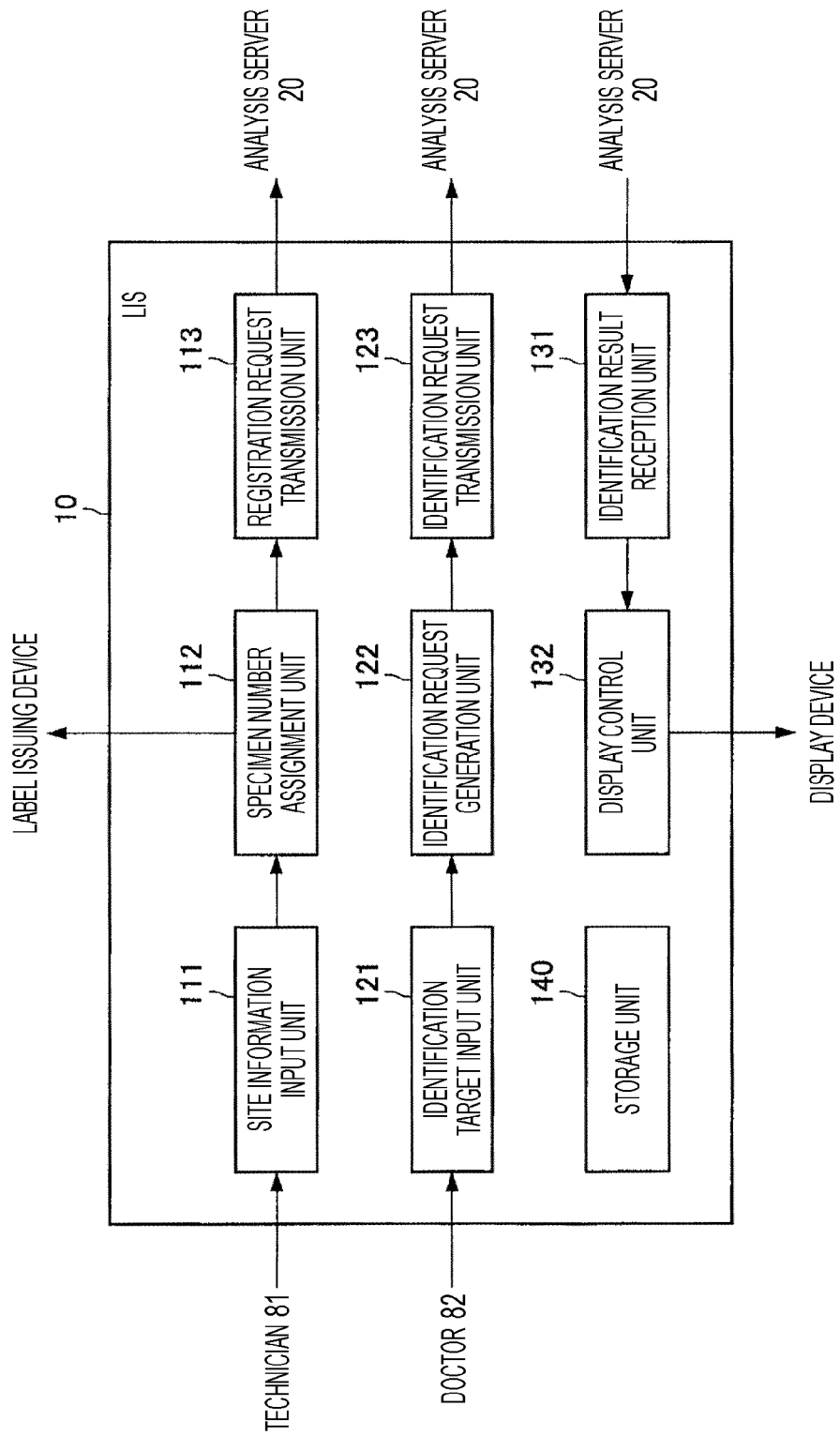
FIG. 2 is a diagram illustrating a functional configuration example of LIS according to the embodiment of the present disclosure.

Next, a functional configuration example of the LIS 10 according to the embodiment of the present disclosure will be described. FIG. 2 is a diagram illustrating a functional configuration example of the LIS 10 according to the embodiment of the present disclosure. As illustrated in FIG. 2, the LIS 10 has a site information input unit 111, a specimen number assignment unit 112, a registration request transmission unit 113, an identification target input unit 121, an identification request generation unit 122, an identification request transmission unit 123, an identification result reception unit 131, a display control unit 132, and a storage unit 140.

The specimen number assignment unit 112, the identification request generation unit 122, and the display control unit 132 may include, for example, a processing device such as one or a plurality of central processing units (CPUs). Such a processing device may include an electronic circuit. The specimen number assignment unit 112, the identification request generation unit 122, and the display control unit 132 can be implemented by executing a program (software) by such a processing device.

The specimen number assignment unit 112 is connected to a label issuing device, which will be described later. Note that in the embodiment of the present disclosure, it is mainly assumed a case where the label issuing device exists outside the LIS 10. However, the label issuing device may be present inside the LIS 10. Furthermore, the display control unit 132 is connected to a display device, which will be described later. Note that in the embodiment of the present disclosure, it is mainly assumed a case where the display device exists outside the LIS 10. However, the display device may exist inside the LIS 10. The display device may be achieved by a display, and the display may be a liquid crystal display, an organic electro-luminescence (EL) display, or another display.

The site information input unit 111 has a function of receiving input of site information by the technician 81. Furthermore, the identification target input unit 121 has a function of receiving input of an identification target by the doctor 82. In the embodiment of the present disclosure, it is mainly assumed a case where the site information input unit 111 and the identification target input unit 121 are achieved by common hardware. However, the site information input unit 111 and the identification target input unit 121 may be achieved by separate hardware. Specifically, the site information input unit 111 and the identification target input unit 121 may include a mouse and a keyboard, a touch panel, a microphone for detecting voice, or an image sensor for detecting a line of sight.

The storage unit 140 is a recording medium that includes a memory and stores a program executed by a processing device and stores data necessary for executing the program. Furthermore, the storage unit 140 temporarily stores data for calculation by the processing device. The storage unit 140 includes a magnetic storage unit device, a semiconductor storage device, an optical storage device, an optical magnetic storage device, or the like.

The registration request transmission unit 113, the identification request transmission unit 123, and the identification result reception unit 131 include a communication circuit. The registration request transmission unit 113 has a function of transmitting a registration request, which will be described later, to the analysis server 20 via the network 71. The identification request transmission unit 123 has a function of transmitting an identification request, which will be described later, to the analysis server 20 via the network 71. The identification result reception unit 131 has a function of receiving an identification result, which will be described later, from the analysis server 20 via the network 71.

The functional configuration example of the LIS 10 according to the embodiment of the present disclosure has been described above.

1.3. Functional Configuration Example of Analysis Server

Figure 3:
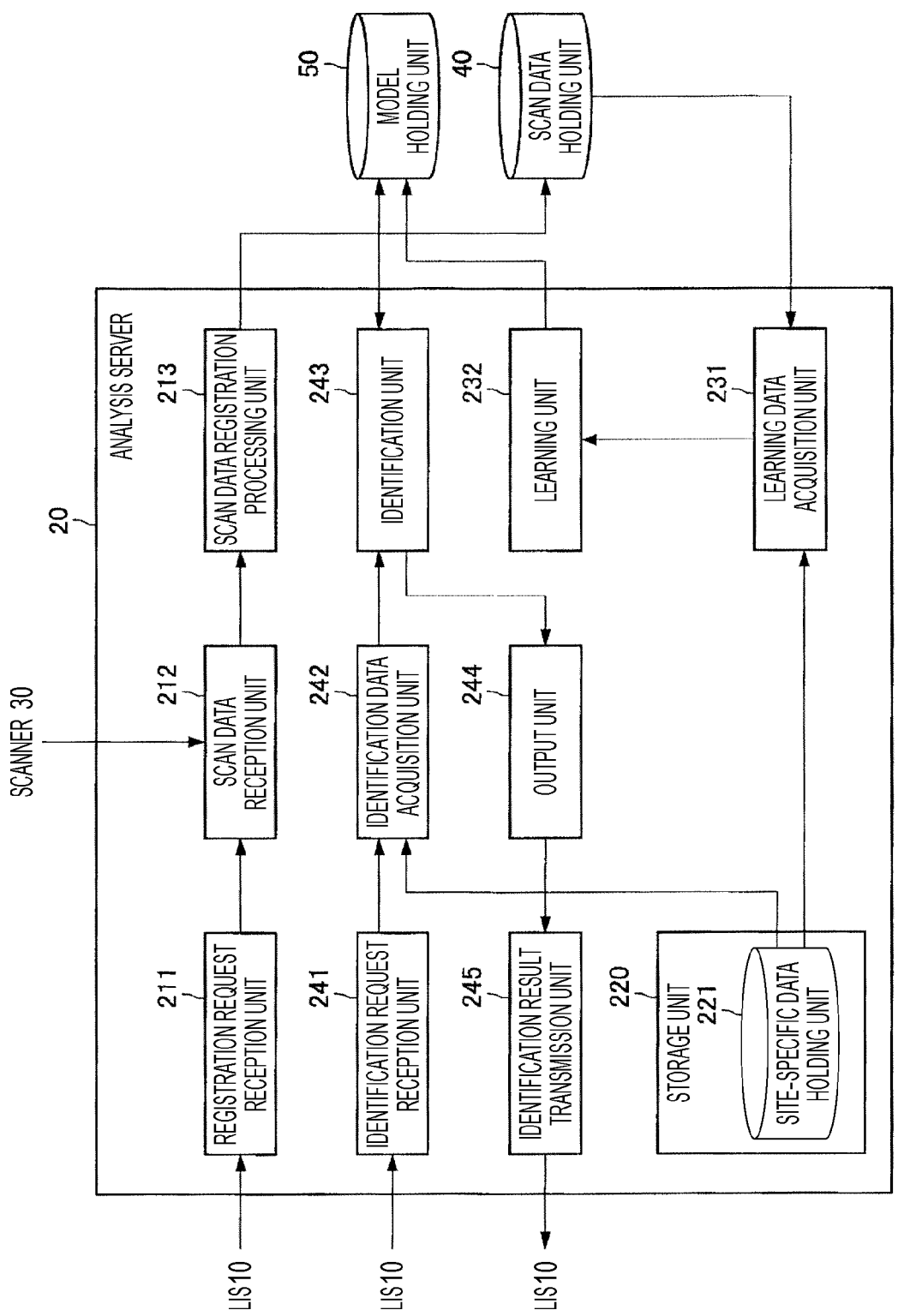
FIG. 3 is a diagram illustrating a functional configuration example of an analysis server according to the embodiment of the present disclosure.

Next, a functional configuration example of the analysis server 20 according to the embodiment of the present disclosure will be described. FIG. 3 is a diagram illustrating a functional configuration example of the analysis server 20 according to the embodiment of the present disclosure. As illustrated in FIG. 3, the analysis server 20 has a registration request reception unit 211, a scan data reception unit 212, a scan data registration processing unit 213, a storage unit 220, an identification request reception unit 241, an identification data acquisition unit 242, an identification unit 243, an output unit 244, an identification result transmission unit 245, a learning data acquisition unit 231, and a learning unit 232.

The scan data registration processing unit 213, the identification data acquisition unit 242, the identification unit 243, the output unit 244, the learning data acquisition unit 231, and the learning unit 232 may include, for example, a processing device such as one or a plurality of CPUs (central processing units) or the like. Such a processing device may include an electronic circuit. The scan data registration processing unit 213, the identification data acquisition unit 242, the identification unit 243, the output unit 244, the learning data acquisition unit 231, and the learning unit 232 are implemented by executing a program (software) by such a processing device.

The scan data registration processing unit 213 and the learning data acquisition unit 231 are connected to the scan data holding unit 40. Further, the identification unit 243 and the learning unit 232 are connected to the model holding unit 50. Furthermore, the identification data acquisition unit 242 and the learning data acquisition unit 231 are connected to a site-specific data holding unit 221, which will be described later.

The storage unit 220 is a recording medium that includes a memory and stores a program executed by a processing device and stores data necessary for executing the program. The storage unit 220 stores site-specific data as an example of the data necessary for executing the program (that is, the storage unit 220 has the site-specific data holding unit 221). Furthermore, the storage unit 220 temporarily stores data for calculation by the processing device. The storage unit 220 includes a magnetic storage unit device, a semiconductor storage device, an optical storage device, an optical magnetic storage device, or the like.

Figures 4, 5:
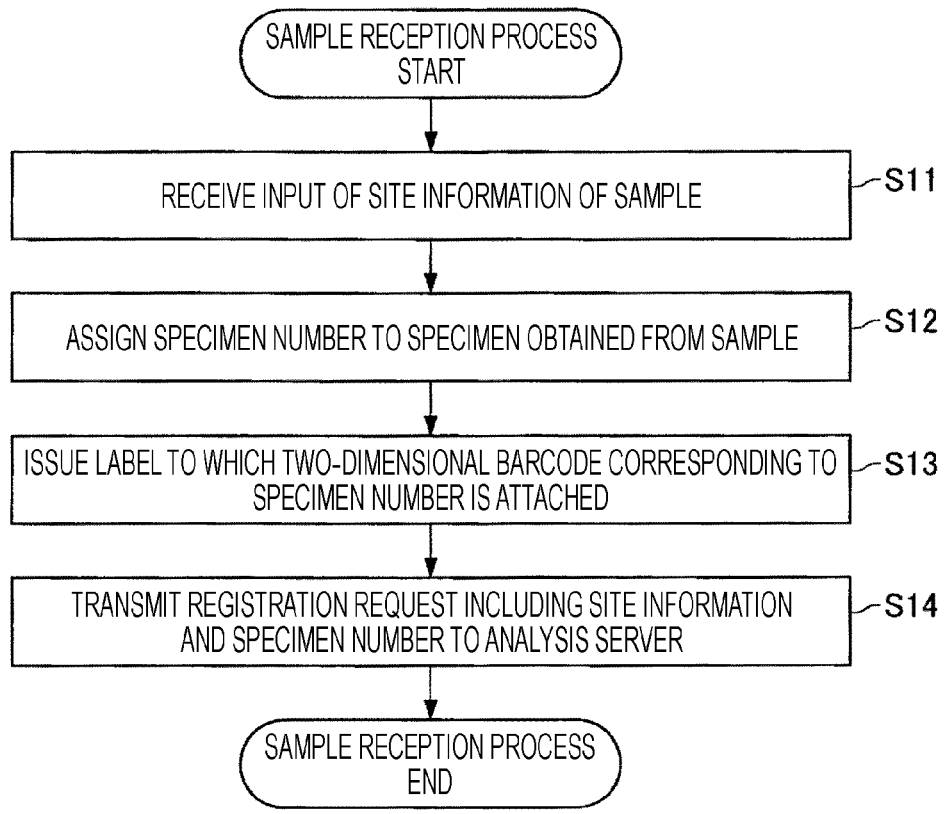
FIG. 4 is a diagram illustrating an example of site-specific data stored by a site-specific data holding unit.
FIG. 5 is a flowchart illustrating a flow of a sample reception process.

FIG. 4 is a diagram illustrating an example of site-specific data stored by the site-specific data holding unit 221. Referring to FIG. 4, three entries (three lines of data) are registered in the site-specific data (stored by the site-specific data holding unit 221). However, the number of entries registered in the site-specific data is not limited. Each entry includes site information, scan data storage location, learner information (information to identify the learner), model information (information for identifying the model), and identifier information (information to identify the identifier), which are associated with each other.

Returning to FIG. 3, the description will be continued. The registration request reception unit 211, the scan data reception unit 212, the identification request reception unit 241, and the identification result transmission unit 245 include a communication circuit. The registration request reception unit 211 has a function of receiving a registration request, which will be described later, from the analysis server 20 via the network 71. The scan data reception unit 212 receives scan data from the scanner 30 via the network 72. The identification request reception unit 241 has a function of receiving an identification request, which will be described later, from the analysis server 20 via the network 71. The identification result transmission unit 245 has a function of transmitting an identification result, which will be described later, to the analysis server 20 via the network 71.

The functional configuration example of the analysis server 20 according to the embodiment of the present disclosure has been described above.

1.4. Details of Functions of System

Next, details of functions possessed by the information processing system 1A according to the embodiment of the present disclosure will be described. First, a sample reception process is executed by the information processing system 1A according to the embodiment of the present disclosure. Thus, the sample reception process will be described.

1.4.1. Sample Reception Process

FIG. 5 is a flowchart illustrating a flow of a sample reception process. First, when the technician obtains a sample and inputs site information of the sample into the LIS 10, as illustrated in FIG. 5, the site information input unit 111 receives the input of the site information of the sample in the LIS 10 (S11). The technician processes the sample and obtains a specimen from the sample. Then, the specimen number assignment unit 112 assigns a specimen number to the specimen obtained from the sample (S12). Here, the specimen number may be information (specimen information) for uniquely identifying the specimen, and the specimen number assignment unit 112 is only required to assign any vacant specimen number to the specimen.

The label issuing device generates a two-dimensional barcode corresponding to the specimen number, and issues (prints) a label to which the two-dimensional barcode is attached (S13). The technician affixes the label issued by the label issuing device to a slide (glass slide).

Note that here it is mainly assumed a case where the two-dimensional barcode corresponding to the specimen number is affixed on the slide instead of characters indicating the specimen number. However, instead of the 2D barcode, another code (for example, 1D barcode or the like) may be affixed on the slide. By affixing the code corresponding to the specimen number on the slide instead of the characters indicating the specimen number in this manner, readability of the specimen number by the scanner 30 is improved.

Alternatively, a label to which letters indicating the specimen number are added may also be issued. That is, the format of the specimen number attached to the label is not limited. Furthermore, here, it is mainly assumed a case where a two-dimensional barcode corresponding to the specimen number is attached to the label. However, in addition to the two-dimensional barcode corresponding to the specimen number, other information may be attached to the label. Also in this case, the format of the other information attached to the label is not limited.

For example, the format of the other information may be a code corresponding to the other information (for example, a one-dimensional barcode, a two-dimensional barcode, or the like), or may be characters indicating the other information. The other information may include site information of which input has been received by the site information input unit 111. Moreover, the technician places the specimen on the slide to which the label is affixed. The slide on which the label is affixed and the specimen is placed is a target of reading by the scanner 30.

Figure 6:
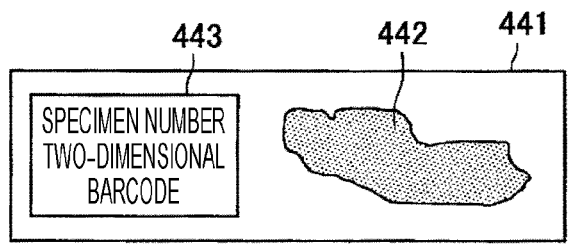
FIG. 6 is a diagram illustrating an example of a slide as a target of reading.

FIG. 6 is a diagram illustrating an example of a slide as a target of reading. As illustrated in FIG. 6, a label 443 to which a two-dimensional barcode corresponding to the specimen number is attached is affixed to a slide 441. Furthermore, a specimen 442 is placed on the slide 441. When the technician causes the scanner 30 to read the slide as a target of reading, the scanner 30 generates scan data. The scan data includes image data of the specimen and image data of the two-dimensional barcode corresponding to the specimen number. Note that as described above, in a case where the site information is also attached to the label, the scan data also includes image data of the site information. The scan data is transmitted from the scanner 30 to the analysis server 20 via the network 72.

Returning to FIG. 5, the description will be continued. The registration request transmission unit 113 transmits a registration request including the site information site information of which input has been received by the site information input unit 111 and the specimen number assigned by the specimen number assignment unit 112 to the analysis server 20 via the network 71 (S14). Note that as described above, in a case where the site information is attached to the label in addition to the specimen number, the registration request transmission unit 113 does not have to transmit the registration request to the analysis server 20.

The sample reception process has been described above. Subsequently, a data registration process is executed by the information processing system 1A according to the embodiment of the present disclosure. Thus, the data registration process will be described.

1.4.2. Data Registration Process

Figure 7:
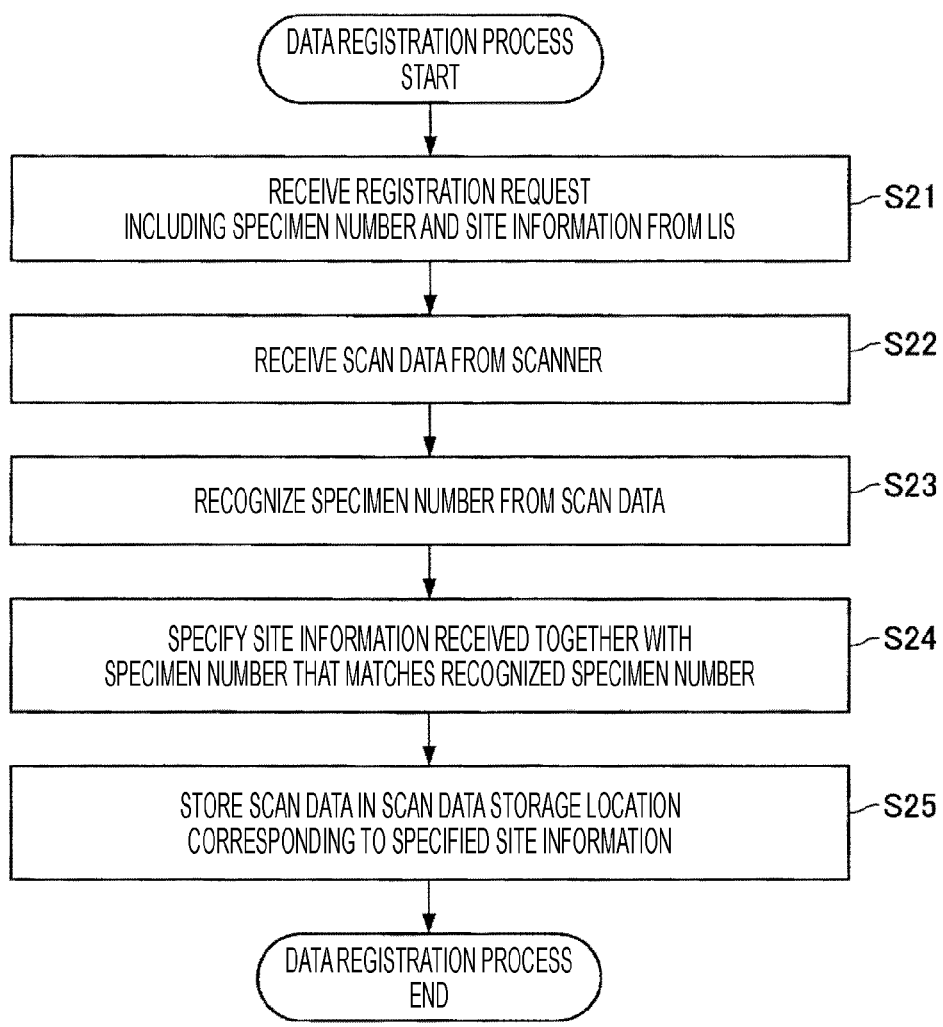
FIG. 7 is a flowchart illustrating a flow of a data registration process.

FIG. 7 is a flowchart illustrating a flow of the data registration process. In the analysis server 20, the registration request reception unit 211 receives the registration request including the site information and the specimen number from the LIS 10 via the network 71 (S21). Then, the scan data reception unit 212 receives the scan data from the scanner 30 via the network 72 (S22). The scan data registration processing unit 213 recognizes the specimen number from the image data of the two-dimensional barcode corresponding to the specimen number included in the scan data (S23).

The scan data registration processing unit 213 specifies the site information received from the LIS 10 together with a specimen number that matches the specimen number recognized from the scan data (S24). More specifically, in a case where the scan data registration processing unit 213 receives a registration request including a specimen number that matches the specimen number recognized from the scan data, the scan data registration processing unit 213 specifies site information included in the registration request. Note that as described above, in a case where the scan data includes the image data of the site information, the scan data registration processing unit 213 may recognize the site information from the image data of the site information. Furthermore, at least one of the specimen number or the site information may be recognized from the scan data by the scanner 30 instead of the analysis server 20.

Subsequently, the scan data registration processing unit 213 saves the scan data in the scan data storage location corresponding to the specified site information with reference to the site-specific data holding unit 221 (FIG. 4) (S25).

The data registration process has been described above. Subsequently, a model generation process will be executed by the information processing system 1A according to the embodiment of the present disclosure. Thus, the model generation process will be described.

1.4.3. Model Generation Process

Figure 8:
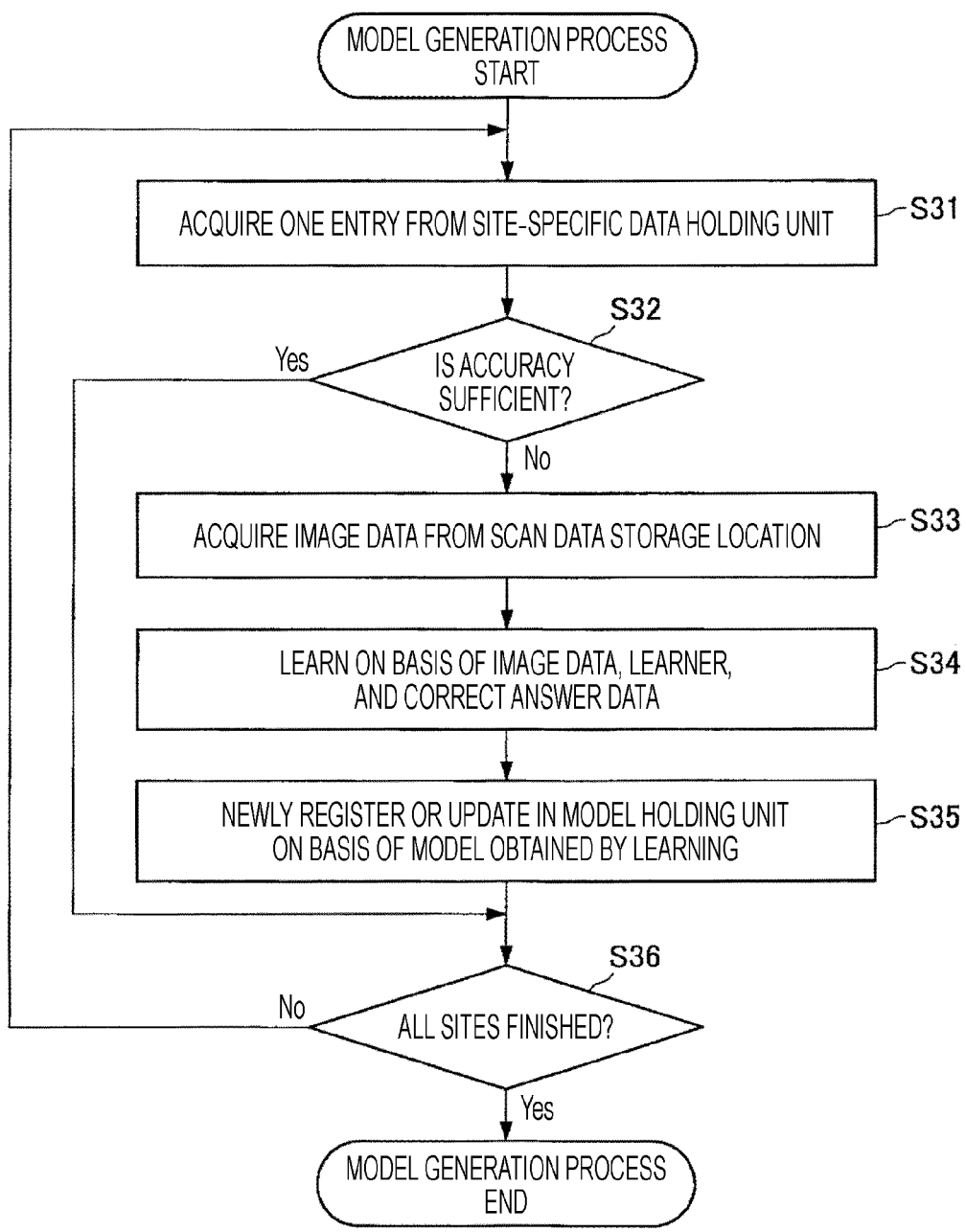
FIG. 8 is a flowchart illustrating a flow of a model generation process.

FIG. 8 is a flowchart illustrating a flow of the model generation process. Note that, here, it is mainly assumed a case where the model generation corresponding to each of all pieces of the site information registered in the site-specific data holding unit 221 (FIG. 4) is sequentially performed in a case where a predetermined timing is detected (for example, periodically or in a case where an instruction of the doctor is input to the LIS 10). However, it is not necessary to generate a model corresponding to each of all pieces of the site information registered in the site-specific data holding unit 221. For example, only model generation corresponding to the site information input by the doctor may be performed. Furthermore, although the above-described model generation process is an example of generating a model in the same system, a model created for every site other than this system may be used.

In the analysis server 20, when the learning data acquisition unit 231 detects a predetermined timing, it acquires one entry from the site-specific data holding unit 221 (S31). One entry includes site information, scan data storage location, learner information, model information, and identifier information. The learning unit 232 determines whether or not accuracy of the model corresponding to the site information is sufficient on the basis of one acquired entry (S32). More specifically, the learning unit 232 determines whether or not to generate a new model on the basis of accuracy of the model in a case where the model corresponding to the site information already exists in the model holding unit 50 on the basis of one acquired entry.

Here, the accuracy of the model may be determined in any way. For example, in a case where the learning unit 232 causes the identifier corresponding to the site information to perform identification with respect to evaluation data on the basis of the model corresponding to the site information, the learning unit 232 may determine the accuracy of the model on the basis of the correct answer rate of the identification result. Then, whether or not the accuracy of the model is sufficient is only required to be determined by whether or not the accuracy of the model is higher than a threshold. In a case where the learning unit 232 determines that the accuracy of the model corresponding to the site information is sufficient ("Yes" in S32), the learning unit 232 advances the operation to S36.

On the other hand, in a case where the learning unit 232 determines that the accuracy of the model corresponding to the site information is not sufficient ("No" in S32), the learning unit 232 acquires the scan data (including image data of specimen) from the scan data storage location (S33). The image data of specimen can correspond to the image data for learning in which a second biological region is captured. Furthermore, the site information may correspond to second site information of the second biological region.

The learning unit 232 selects the learner corresponding to the site information on the basis of one acquired entry. Then, the learning unit 232 generates a model corresponding to the site information (by performing learning) on the basis of the image data of the specimen and the selected learner. More specifically, in a case where correct answer data is associated with the image data of the specimen, the learning data acquisition unit 231 acquires the correct answer data, and the learning unit 232 generates a model on the basis of (by learning) the image data of the specimen, the selected learner, and the correct answer data (S34).

If the model is generated by the learner prepared for every site in this manner, resources (time or hardware resources) necessary for generating the model used for the identifier can be reduced as compared with the case where one model corresponding to a plurality of sites is generated.

The learning unit 232 performs new registration or update in the model holding unit 50 on the basis of the generated model (S35). More specifically, in a case where the model corresponding to the site information does not exist in the model holding unit 50, the learning unit 232 newly registers the generated model in association with the site information in the model holding unit 50. On the other hand, in a case where the model corresponding to the site information already exists in the model holding unit 50, the learning unit 232 updates the model already associated with the site information in the model holding unit 50 with the generated model.

In a case where the model generation corresponding to each of all or part of pieces of the site information registered in the site-specific data holding unit 221 (FIG. 4) has not been finished ("No" in S36), the learning data acquisition unit 231 acquires a next entry from the site-specific data holding unit 221 (FIG. 4) (S31), and the operation is advanced to S32. On the other hand, in a case where the model generation corresponding to each of all pieces of the site information registered in the site-specific data holding unit 221 (FIG. 4) has been finished ("Yes" in S36), the model generation process is finished.

The model generation process has been described above. Subsequently, a display process is executed by the information processing system 1A according to the embodiment of the present disclosure. Thus, the display process will be described.

1.4.4. Display Process

Figure 9:
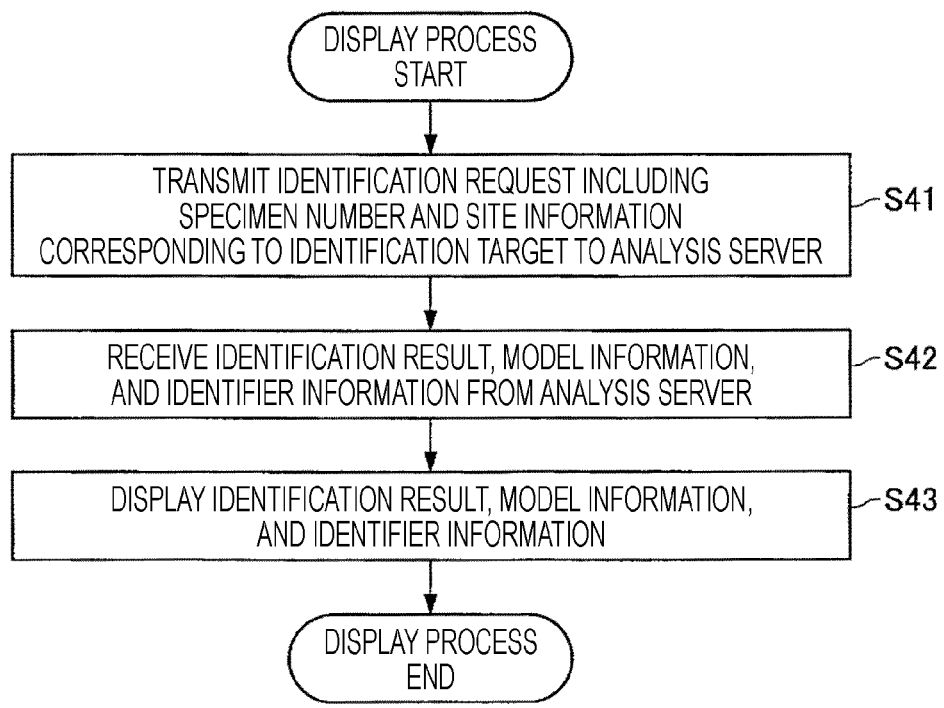
FIG. 9 is a flowchart illustrating a flow of a display process.

FIG. 9 is a flowchart illustrating a flow of the display process. First, the doctor inputs the specimen number corresponding to the identification target (specimen) and the site information of the specimen into the LIS 10. Then, the identification target input unit 121 receives input of the specimen number and the site information. The identification request generation unit 122 generates an identification request including the specimen number and the site information of which input has been received by the identification target input unit 121. Then, the identification request transmission unit 123 transmits the identification request including the specimen number and the site information corresponding to the identification target (specimen) to the analysis server 20 via the network 71 (S41).

Note that, here, it is assumed a case where both the specimen number and the site information are input to the LIS 10 by the doctor. However, as long as the analysis server 20 can grasp the correspondence between the specimen number and the site information of the specimen, the site information does not have to be input by the doctor, and the identification request does not have to include the specimen number. Furthermore, the specimen number and the site information may be input to the analysis server 20 without going through the LIS 10. Subsequently, the analysis server 20 performs an identification process in response to the identification request. Such identification process will be described later with reference to FIG. 10.

The identification result reception unit 131 receives an identification result in response to the identification request, model information used for identification (information for identifying the model used for identification), and the identifier information used for identification (information for identifying the identifier used for identification) from the analysis server 20 via the network 71 (S42). The display control unit 132 controls the display device so that the identification result, the model information, and the identifier information received by the identification result reception unit 131 are displayed by the display device (S43).

Note that in a case where the learner information (information regarding the learner) used for model generation is received from the analysis server 20, the display device may be controlled so that the learner information is also displayed by the display device. Thus, the doctor can understand what kind of learner is used for model generation. The identification result will be described later with reference to FIG. 10.

The display process has been described above. Next, an identification process executed by the information processing system 1A according to the embodiment of the present disclosure will be described.

1.4.5. Identification Process

Figure 10:
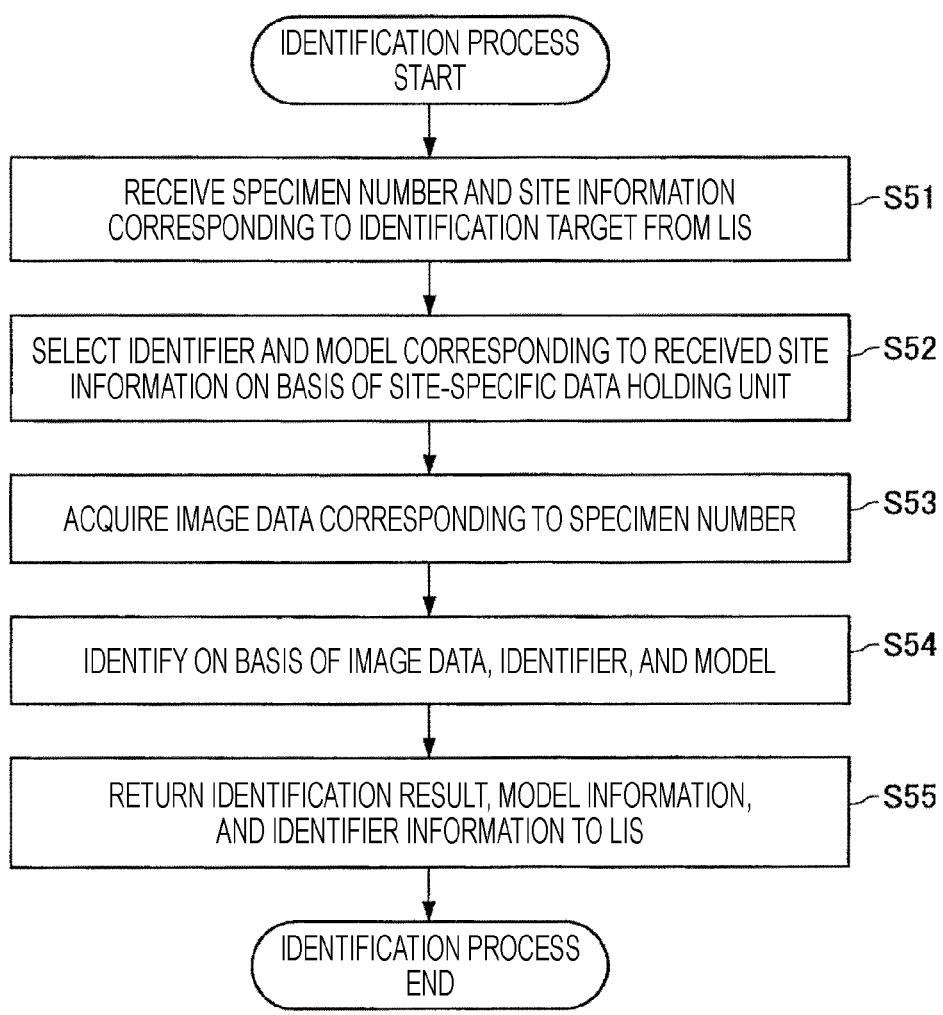
FIG. 10 is a flowchart illustrating a flow of an identification process.

FIG. 10 is a flowchart illustrating a flow of an identification process. First, the identification request reception unit 241 receives the identification request including a specimen number and site information corresponding to the identification target (specimen) from the LIS 10 via the network 71 (S51). The identification data acquisition unit 242 acquires the received site information. On the basis of the site-specific data holding unit 221 (FIG. 4), the identifier and model corresponding to the site information are selected (S52). Furthermore, the identification data acquisition unit 242 acquires scan data from the scan data storage location corresponding to the site information on the basis of the site-specific data holding unit 221 (FIG. 4), and acquires image data of the specimen corresponding to the received specimen number from the scan data (S53).

More specifically, the identification data acquisition unit 242 acquires the image data of the specimen from the scan data in which the specimen number matching the received specimen number is recognized. The image data of the specimen may correspond to the image data for identification in which the first biological region is captured. Furthermore, the site information may correspond to the first site information of the first biological region.

The identification unit 243 selects the identifier corresponding to the received site information from the identifiers existing in the model holding unit 50. Then, the identification unit 243 performs the identification process on the basis of the image data of the specimen and the selected identifier. If the identifier prepared for every site is used for the identification process in this manner, it is possible to improve the accuracy of the identification process based on image data for identification in which a biological region is captured. More specifically, the identification unit 243 performs the identification process on the basis of the image data of the specimen, the selected identifier, and the selected model (S54).

Here, the identification result is not particularly limited. For example, the identification result may include a diagnostic result corresponding to the biological region (first biological region), an analysis result corresponding to the biological region, or both the diagnostic result and the analysis result. Furthermore, the diagnostic result is not limited. For example, the diagnostic result may include information regarding whether or not a subject having the biological region in a body has cancer. Furthermore, the diagnostic results may also include information regarding the cancer (cancer subtype, cancer stage, degree of differentiation of cancer cells, and the like). The degree of differentiation can be used to predict information such as what kind of drug (anticancer drug, or the like) is likely to work.

The analysis result is also not limited. For example, the analysis result may include at least one of the presence or absence of a lesion in the biological region, the probability that a lesion is included in the biological region, the location of the lesion, or the type of the lesion.

Subsequently, the output unit 244 outputs the identification result obtained by the identification process, the model information used for the identification, and the identifier information used for the identification. The identification result transmission unit 245 returns the identification result, the model information, and the identifier information to the LIS 10 via the network 71 (S55). Note that the output unit 244 may output the learner information (information regarding the learner) used to generate the model used by the identifier. In such a case, the identification result transmission unit 245 may return the learner information to the LIS 10 via the network 71 in addition to the identification result, the model information, and the identifier information.

The identification process has been described above.

The details of the functions possessed by the information processing system 1A according to the embodiment of the present disclosure have been described above.

2. Modification Example

Next, various modification examples will be described.

Hereinafter, modification example 1 will be described. In the foregoing, it is assumed a case where the learner, the identifier, and the model are associated with the site information. However, it is also assumed a case where the learner, the identifier, and the model are associated with a combination of site information and other information. For example, it is assumed that what kind of drug is likely to work on cells changes according to how much the cells are expressed with respect to which staining reagent. Therefore, the learner, the identifier, and the model may be associated with a combination of site information and staining information (information indicating the type of staining reagent). The combination of the site information and the staining information may be any combination.

As an example, a combination of site information indicating "stomach" and staining information indicating "hematoxylin/eosin (HE) staining" is assumed. Furthermore, a combination of site information indicating "stomach" and staining information indicating "immunohistochemistry=IHC" is assumed. The immunohistochemistry (IHC) may include immunohistochemistry (IHC) of estrogen receptor (ER) or immunohistochemistry (IHC) of progesterone receptor (PR).

At this time, the model holding unit 50 stores the learner, the identifier, and the model corresponding to the site information and the staining information. Then, the site-specific data holding unit 221 stores the scan data storage location, the learner information, the model information, and the identifier information in response to the combination of the site information and the staining information.

Then, in the model generation process, the learning data acquisition unit 231 acquires staining information (second staining information) in addition to the site information (second site information) from the site-specific data holding unit 221. The learning unit 232 selects a learner corresponding to the site information (second site information) and the staining information (second staining information) with reference to the site-specific data holding unit 221. The learning unit 232 generates a model on the basis of the selected learner and the image data (image data for learning) of the specimen acquired from the scan data.

Furthermore, in the identification process, the identification data acquisition unit 242 acquires staining information (first staining information) in addition to site information (first site information) from the identification request received from the LIS 10. The identification unit 243 selects an identifier corresponding to the site information (first site information) and staining information (first staining information) with reference to the site-specific data holding unit 221. The identification unit 243 performs an identification process on the basis of the selected identifier and the image data (image data for identification) of the specimen acquired from the scan data.

Figure 11:
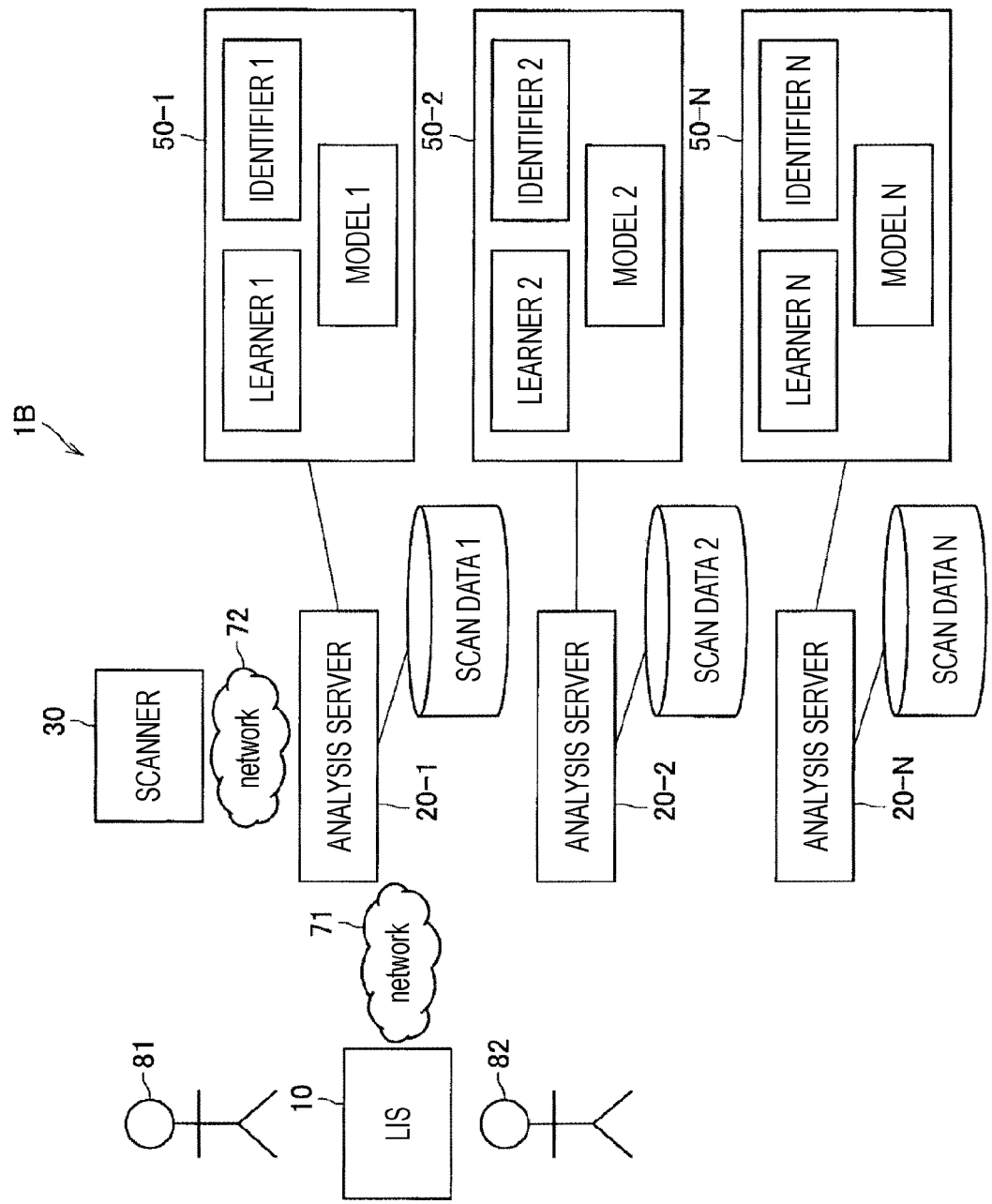
FIG. 11 is a diagram illustrating a configuration example of an information processing system according to modification example 2.

Next, modification example 2 will be described. FIG. 11 is a diagram illustrating a configuration example of an information processing system according to modification example 2. In the foregoing, as illustrated in FIG. 1, it is assumed a case where the information processing system 1A has one analysis server 20, and one analysis server 20 executes the model generation and identification process corresponding to each of all pieces of site information. On the other hand, in second modification example 2, as illustrated in FIG. 11, it is assumed a case where the information processing system 1B has a plurality of analysis servers 20 (analysis servers 20-1 to 20-N), and each of the plurality of analysis servers 20 executes the model generation and identification process corresponding to one piece of site information.

Therefore, in the second modification example, as illustrated in FIG. 11, scan data 1 and the model holding unit 50-1 (learner 1, identifier 1, model 1) are connected to the analysis server 20-1, and scan data 2 and the model holding unit 50-2 (learner 2, identifier 2, model 2) are connected to the analysis server 20-2, and . . . , scan data N and the model holding unit 50-N (learner N, identifier N, model N) are connected to the analysis server 20-N. Furthermore, a site-specific data holding unit 141 (FIG. 12) is stored.

Figure 12:
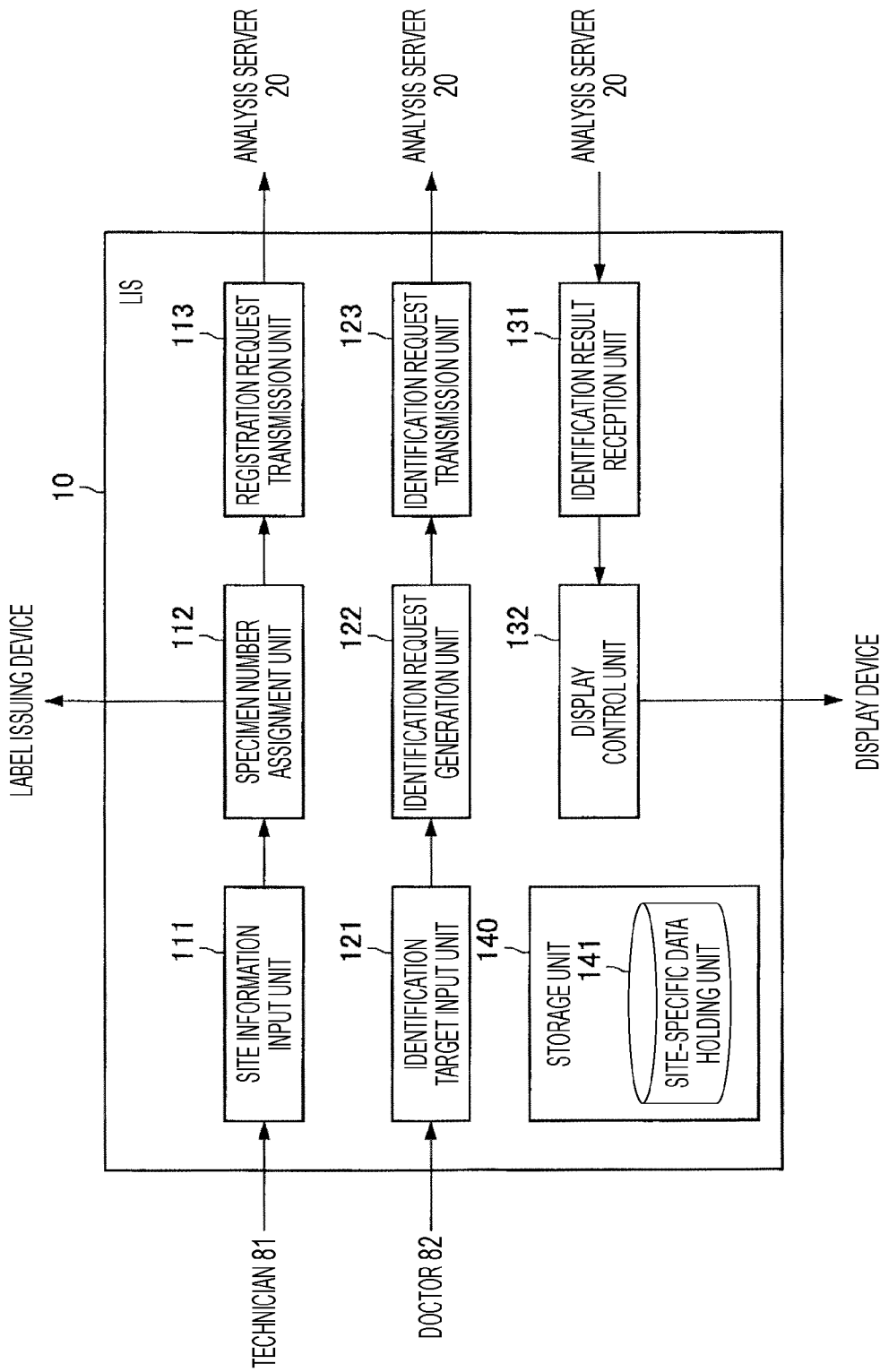
FIG. 12 is a diagram illustrating a functional configuration example of LIS according to modification example 2.

FIG. 12 is a diagram illustrating a functional configuration example of the LIS 10 according to the modification example 2. As illustrated in FIG. 12, each of the plurality of analysis servers 20 has the site-specific data holding unit 141. FIG. 13 is a diagram illustrating an example of the site-specific data stored by the site-specific data holding unit 141 according to the modification example 2. Referring to FIG. 13, each entry includes site information and an analysis server associated with each other. By referring to the site-specific data holding unit 141, the LIS 10 can grasp which analysis server 20 executes the model generation and identification process corresponding to the site information. That is, the LIS 10 can select the analysis server 20 to which the registration request and the identification request have to be transmitted by referring to the site-specific data holding unit 141.

The various modification examples have been described above.

3. Hardware Configuration Example

Figure 14:
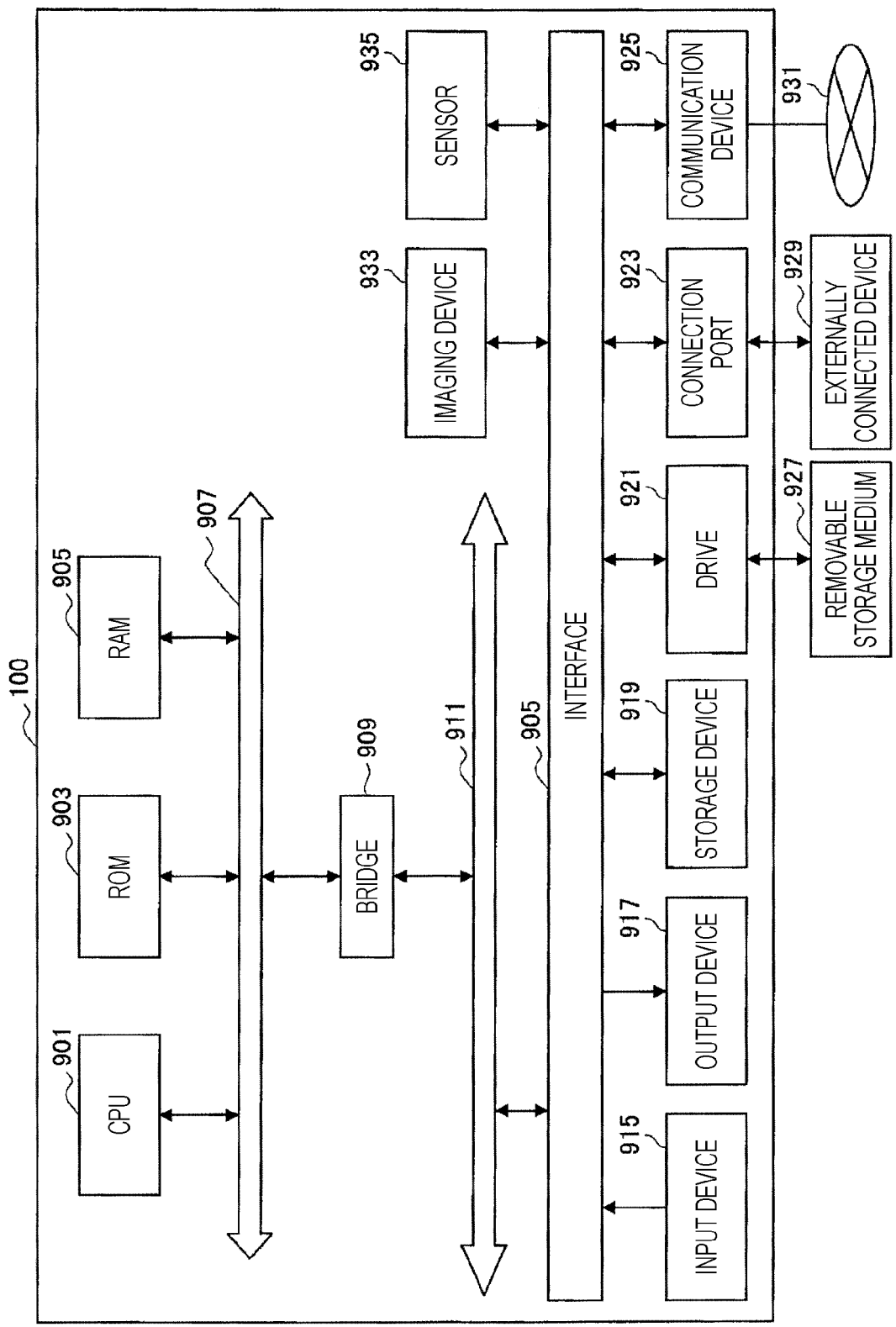
FIG. 14 is a block diagram illustrating a hardware configuration example of an analysis server according to the embodiment of the present disclosure.

Next, a hardware configuration example of the analysis server 20 according to the embodiment of the present disclosure will be described with reference to FIG. 14. FIG. 14 is a block diagram illustrating a hardware configuration example of the analysis server 20 according to the embodiment of the present disclosure. Note that the analysis server 20 does not necessarily have all of the hardware configurations illustrated in FIG. 14, and a part of the hardware configuration illustrated in FIG. 14 does not necessarily exist in the analysis server 20. Furthermore, the hardware configuration of the LIS 10 may be achieved similarly to the hardware configuration of the analysis server 20.

As illustrated in FIG. 14, the analysis server 20 includes a central processing unit (CPU) 901, a read only memory (ROM) 903, and a random access memory (RAM) 905. Furthermore, the analysis server 20 may include a host bus 907, a bridge 909, an external bus 911, an interface 913, an input device 915, an output device 917, a storage device 919, a drive 921, a connection port 923, and a communication device 925. Moreover, the analysis server 20 may include an imaging device 933 and a sensor 935, if necessary. The analysis server 20 may have a processing circuit called a digital signal processor (DSP) or an application specific integrated circuit (ASIC) in place of or in combination with the CPU 901.

The CPU 901 functions as an arithmetic processing device and a control device, and controls overall operations or a part thereof in the analysis server 20 in accordance with various programs recorded in the ROM 903, the RAM 905, the storage device 919, or a removable recording medium 927. The ROM 903 stores programs and calculation parameters and the like used by the CPU 901. The RAM 905 temporarily stores a program used in execution by the CPU 901, parameters that change as appropriate during the execution, and the like. The CPU 901, ROM 903, and RAM 905 are connected to each other by a host bus 907 including an internal bus such as a CPU bus. Moreover, the host bus 907 is connected to the external bus 911 such as a peripheral component interconnect/interface (PCI) bus via the bridge 909.

The input device 915 is, for example, a device operated by the user, such as a button. The input device 915 may include a mouse, a keyboard, a touch panel, switches, levers, and the like. Furthermore, the input device 915 may also include a microphone that detects voice of the user. The input device 915 may be, for example, a remote control device using infrared rays or other radio waves, or an externally connected device 929 such as a mobile phone corresponding to the operation of the analysis server 20. The input device 915 includes an input control circuit that generates an input signal on the basis of information input by the user and outputs the input signal to the CPU 901. By operating this input device 915, the user inputs various data and instructs the analysis server 20 on a processing operation. Furthermore, the imaging device 933 as described later can also function as an input device by capturing an image of movement of a hand of the user, a finger of the user, or the like. At this time, a pointing position may be determined according to movement of the hand or the direction of the finger.

The output device 917 includes a device that can visually or audibly notify the user of acquired information. The output device 917 may be, for example, a display device such as a liquid crystal display (LCD) or an organic electro-luminescence (EL) display, a sound output device such as a speaker or headphones, and the like. Furthermore, the output device 917 may include a plasma display panel (PDP), a projector, a hologram, a printer device, and the like. The output device 917 outputs a result obtained by processing of the analysis server 20 as a video such as text or an image, or as an audio such as voice or sound. Furthermore, the output device 917 may include a light or the like in order to brighten the surroundings.

The storage device 919 is a device for storing data, which is formed as an example of a storage unit of the analysis server 20. The storage device 919 includes, for example, a magnetic storage device such as a hard disk drive (HDD), a semiconductor storage device, an optical storage device, an optical magnetic storage device, or the like. The storage device 919 stores programs and various data executed by the CPU 901, various data acquired from the outside, and the like.

The drive 921 is a reader-writer for a removable recording medium 927 such as a magnetic disk, an optical disk, a magneto-optical disk, or a semiconductor memory, and is built in or externally attached to the analysis server 20. The drive 921 reads information recorded in the mounted removable recording medium 927 and outputs the information to the RAM 905. Furthermore, the drive 921 writes a record to the attached removable recording medium 927.

The connection port 923 is a port for directly connecting a device to the analysis server 20. Examples of the connection port 923 include a universal serial bus (USB) port, an IEEE 1394 port, a small computer system interface (SCSI) port, and the like. Furthermore, the connection port 923 may be an RS-232C port, an optical audio terminal, a High-Definition Multimedia Interface (registered trademark) (HDMI) port, or the like. By connecting the externally connected device 929 to the connection port 923, various data can be exchanged between the analysis server 20 and the externally connected device 929.

The communication device 925 is, for example, a communication interface including a communication device for connecting to a network 931, or the like. The communication device 925 is, for example, a communication card for a wired or wireless local area network (LAN), Bluetooth (registered trademark), or wireless USB (WUSB), or the like. Furthermore, the communication device 925 may be a router for optical communication, a router for asymmetric digital subscriber line (ADSL), a modem for various communication, or the like. For example, the communication device 925 transmits and receives signals and the like to and from the Internet and other communication devices using a predetermined protocol such as TCP/IP. Furthermore, the network 931 connected to the communication device 925 may be a network connected by wire or wirelessly, and may be, for example, the Internet, a home LAN, infrared communication, radio wave communication, or satellite communication, or the like.

The imaging device 933 uses, for example, an imaging element such as a CCD (charge coupled device) or complementary metal oxide semiconductor (CMOS), and is a device that captures a real space and generates a captured image using various members such as a lens for controlling image formation of a subject image on the imaging element. The imaging device 933 may capture a still image or may capture a moving image.

The sensor 935 is, for example, various sensors such as a distance measuring sensor, an acceleration sensor, a gyro sensor, a geomagnetic sensor, a vibration sensor, an optical sensor, and a sound sensor. The sensor 935 acquires, for example, information regarding the state of the analysis server 20 itself, such as a posture of a housing of the analysis server 20, and information regarding the surrounding environment of the analysis server 20, such as brightness and noise around the analysis server 20. Furthermore, the sensor 935 may also include a global positioning system (GPS) sensor that receives a GPS signal to measure the latitude, longitude, and altitude of the device.

4. Conclusion

According to an embodiment of the present disclosure, there is provided an information processing device including an identification data acquisition unit that acquires image data for identification in which a first biological region is captured and first site information of the first biological region, and an identification unit that selects an identifier corresponding to the first site information from identifiers associated respectively with a plurality of pieces of site information, and performs an identification process on the basis of the identifier and the image data for identification. If the identifier prepared for every site is used for the identification process in this manner, it is possible to improve the accuracy of the identification process based on image data for identification in which a biological region is captured.

Furthermore, the information processing device may further include a learning data acquisition unit that acquires image data for learning in which a second biological region is captured and second site information of the second biological region, and a learning unit that selects a learner corresponding to the second site information from learners associated respectively with the plurality of pieces of site information, and generates model data corresponding to the second site information among pieces of model data associated respectively with the plurality of pieces of site information on the basis of the learner and the image data for learning. If the model is generated by the learner prepared for every site in this manner, resources (time or hardware resources) necessary for generating the model used for the identifier can be reduced as compared with the case where one model corresponding to a plurality of sites is generated.

The preferred embodiments of the present disclosure have been described above in detail with reference to the accompanying drawings, but the technical scope of the present disclosure is not limited to such examples. It is apparent that a person having ordinary knowledge in the technical field of the present disclosure can devise various change examples or modification examples within the scope of the technical idea described in the claims, and it will be naturally understood that they also belong to the technical scope of the present disclosure.

For example, in the foregoing, the information processing system having the LIS 10, the analysis server 20, the scanner 30, the network 71, the network 72, the scan data holding unit 40, and the model holding unit 50 has been mainly described. However, an information processing system having a part of these may also be provided. For example, an information processing system having a part or all of the LIS 10, the analysis server 20, and the scanner 30 may be provided. At this time, the information processing system does not have to be a combination of the entire device (combination of hardware and software).

For example, an information processing system having a first device (combination of hardware and software) and software of a second device among the LIS 10, the analysis server 20, and the scanner 30 may be provided. As an example, an information processing system having the scanner 30 (combination of hardware and software) and the software of the analysis server 20 may also be provided. As described above, according to the embodiment of the present disclosure, an information processing system including a plurality of configurations arbitrarily selected from the LIS 10, the analysis server 20, and the scanner 30 can also be provided.

Furthermore, the effects described in the present description are merely illustrative or exemplary and are not limited. That is, the technology according to the present disclosure can exhibit other effects that are apparent to those skilled in the art from the present description in addition to or instead of the effects described above.

Note that configurations as follows also belong to the technical scope of the present disclosure.

(1)

An information processing device including:

an identification data acquisition unit that acquires image data for identification in which a first biological region is captured and first site information of the first biological region; and an identification unit that selects an identifier corresponding to the first site information from identifiers associated respectively with a plurality of pieces of site information, and performs an identification process on the basis of the identifier and the image data for identification.

(2)

The information processing device according to (1) above, further including an output unit that outputs an identification result obtained by the identification process.

(3)

The information processing device according to (2) above, in which the identification result includes at least one of a diagnostic result or an analysis result corresponding to the first biological region.

(4)

The information processing device according to (3) above, in which the diagnostic result includes information regarding whether or not a subject having the first biological region in a body has a disease.

(5)

The information processing device according to (3) or (4) above, in which the analysis result includes at least one of presence or absence of a lesion in the first biological region, a probability that a lesion is included in the first biological region, a location of the lesion, or a type of the lesion.

(6)

The information processing device according to any one of (2) to (5) above, in which the output unit outputs information regarding a learner used to generate model data used by the identifier.

(7)

The information processing device according to any one of (2) to (5) above, in which the identification data acquisition unit acquires first staining information, and the identification unit selects an identifier corresponding to the first site information and the first staining information from identifiers associated respectively with a plurality of combinations of site information and staining information, and performs the identification process on the basis of the identifier and the image data for identification.

(8)

The information processing device according to any one of (1) to (7) above, in which in a case where scan data including the image data for identification is acquired from a reading device, the identification data acquisition unit acquires the image data for identification on the basis of the scan data.

(9)

The information processing device according to (8) above, in which in a case where the scan data including the first site information is acquired from the reading device, the first site information is recognized on the basis of the scan data.

(10)

The information processing device according to (8) above, in which in a case where the scan data including first specimen information is acquired from the reading device, the first specimen information is recognized from the scan data, and the first site information corresponding to the first specimen information is acquired from another information processing device.

(11)

The information processing device according to any one of (1) to (10) above, in which the identifier is implemented by a neural network, a random forest, a support vector machine, or AdaBoost.

(12)

The information processing device according to any one of (1) to (11) above, in which the first site information is information in which the first biological region is classified into clinically meaningful predetermined units.

(13)

The information processing device according to (12) above, in which the units are one of an organ system, an organ, a tissue, and a disease code.

(14)

The information processing device according to any one of (1) to (13) above, further including:

a learning data acquisition unit that acquires image data for learning in which a second biological region is captured and second site information of the second biological region; and a learning unit that selects a learner corresponding to the second site information from learners associated respectively with the plurality of pieces of site information, and generates model data corresponding to the second site information among pieces of model data associated respectively with the plurality of pieces of site information on the basis of the learner and the image data for learning.

(15)

The information processing device according to (14) above, in which the learning data acquisition unit acquires correct answer data corresponding to the image data for learning, and the learning unit generates the model data on the basis of the learner, the image data for learning, and the correct answer data.

(16)

The information processing device according to (14) or (15) above, in which the learning data acquisition unit acquires second staining information, and the learning unit selects a learner corresponding to the second site information and the second staining information, and generates the model data on the basis of the learner and the image data for learning.

(17)

The information processing device according to any one of (14) to (16) above, in which in a case where the model data corresponding to the second site information already exists, the learning unit determines whether or not to newly generate the model data on the basis of accuracy of the model data.

(18)

An information processing method including:

acquiring, by a processor, image data for identification in which a first biological region is captured and first site information of the first biological region; and selecting, by the processor, an identifier corresponding to the first site information from identifiers associated respectively with a plurality of pieces of site information, and performing, by the processor, an identification process on the basis of the identifier and the image data for identification.

(19)

An information processing system including an information processing device, in which the information processing device includes:

an imaging unit that captures an image of a first biological region;

an identification data acquisition unit that acquires image data of the first biological region captured by the imaging unit and first site information of the first biological region; and an identification unit that selects an identifier corresponding to the first site information from identifiers associated respectively with a plurality of pieces of site information, and performs an identification process on the basis of the identifier and the image data.

(20)

An information processing system including a medical image imaging device and software used for processing image data corresponding to an object imaged by the medical image imaging device, in which the software causes an information processing device to execute an identification process based on first image data corresponding to a first biological region and an identifier corresponding to the first site information of the first biological region.

(21)

An information processing device including:

a learning data acquisition unit that acquires image data for learning in which a second biological region is captured and second site information of the second biological region; and a learning unit that selects a learner corresponding to the second site information from learners associated respectively with a plurality of pieces of site information, and generates model data corresponding to the second site information among pieces of model data associated respectively with the plurality of pieces of site information on the basis of the learner and the image data for learning.

(22)

The information processing device according to (21) above, in which the learning data acquisition unit acquires correct answer data corresponding to the image data for learning, and the learning unit generates the model data on the basis of the learner, the image data for learning, and the correct answer data.

(23)

The information processing device according to (21) or (22) above, in which the learning data acquisition unit acquires second staining information, and the learning unit selects a learner corresponding to the second site information and the second staining information, and generates the model data on the basis of the learner and the image data for learning.

(24)

The information processing device according to any one of (21) to (23) above, in which in a case where the model data corresponding to the second site information already exists, the learning unit determines whether or not to newly generate the model data on the basis of accuracy of the model data.

REFERENCE SIGNS LIST 1A, 1B Information processing system
10 LIS
111 Site information input unit
112 Specimen number assignment unit
113 Registration request transmission unit
121 Identification target input unit
122 Identification request generation unit
123 Identification request transmission unit
131 Identification result reception unit
132 Display control unit
140 Storage unit
141 Site-specific data holding unit
20 Analysis server
211 Registration request reception unit
212 Scan data reception unit
213 Scan data registration processing unit
220 Storage unit
221 Site-specific data holding unit
231 Learning data acquisition unit
232 Learning unit
241 Identification request reception unit
242 Identification data acquisition unit
243 Identification unit
244 Output unit
245 Identification result transmission unit
30 Scanner
40 Scan data holding unit
441 Slide
442 Specimen
443 Label
50 Model holding unit
71 Network
70 Network

The invention claimed is:

1. A first information processing device, comprising:
circuitry configured to:
acquire first image data of an identification target, wherein the first image data includes a first biological region of the identification target;
acquire first site information of a plurality of pieces of site information, wherein
the first site information is associated with the first biological region, and
each piece of site information of the plurality of pieces of site information is associated with a respective identifier of a plurality of identifiers;
select, from the plurality of identifiers, a first identifier corresponding to the acquired first site information;
execute an identification process based on each of the selected first identifier and the acquired first image data;
acquire second image data of the identification target, wherein the second image data includes a second biological region of the identification target;
acquire second site information of the plurality of pieces of site information, wherein
the second site information is associated with the second biological region,
each piece of site information of the plurality of pieces of site information is associated with a respective piece of model data of a plurality of pieces of model data, and
each piece of site information of the plurality of pieces of site information is associated with a respective learner of a plurality of learners;
select, from the plurality of learners, a first learner corresponding to the acquired second site information; and
generate model data, of the plurality of pieces of model data, corresponding to the acquired second site information, wherein the model data is generated based on each of the selected first learner and the acquired second image data.

2. The first information processing device according to claim 1, wherein the circuitry is further configured to output an identification result based on the execution of the identification process.

3. The first information processing device according to claim 2, wherein the identification result includes at least one of a diagnostic result corresponding to the first biological region or an analysis result corresponding to the first biological region.

4. The first information processing device according to claim 3, wherein
the diagnostic result includes information regarding whether a subject has a disease, and
the subject has a body including the first biological region.

5. The first information processing device according to claim 3, wherein the analysis result includes information indicating at least one of:
one of presence of a lesion in the first biological region or absence of the lesion in the first biological region,
a probability that the first biological region includes the lesion,
a location of the lesion, or
a type of the lesion.

6. The first information processing device according to claim 2, wherein the circuitry is further configured to output information regarding the selected first learner.

7. The first information processing device according to claim 2, wherein the circuitry is further configured to:
acquire first staining information of a plurality of pieces of staining information;
select, from the plurality of identifiers, a second identifier corresponding to each of the first site information and the first staining information, wherein each identifier of the plurality of identifiers is associated with a respective combination of a plurality of combinations of the plurality of pieces of site information and the plurality of pieces of staining information; and
perform the identification process based on the second identifier and the first image data.

8. The first information processing device according to claim 1, wherein the circuitry is further configured to:
acquire, from a reading device, scan data including the first image data; and
acquire the first image data based on the acquired scan data.

9. The first information processing device according to claim 8, wherein
the acquired scan data further includes the first site information, and
the circuitry is further configured to recognize the first site information based on the acquired scan data.

10. The first information processing device according to claim 8, wherein
the acquired scan data further includes first specimen information, and
the circuitry is further configured to:
recognize the first specimen information from the acquired scan data; and
acquire the first site information corresponding to the first specimen information from a second information processing device.

11. The first information processing device according to claim 1, wherein implementation of the first identifier is based on at least one of a neural network, a random forest, a support vector machine, or AdaBoost.

12. The first information processing device according to claim 1, wherein the first site information includes information indicating that the first biological region is classified into clinically meaningful units.

13. The first information processing device according to claim 12, wherein each of the clinically meaningful units is at least one of an organ system, an organ, a tissue, or a disease code.

14. The first information processing device according to claim 1, wherein the circuitry is further configured to:
acquire correct answer data corresponding to the second image data; and
generate the model data based on the correct answer data.

15. The first information processing device according to claim 1, wherein the circuitry is further configured to:
acquire second staining information;
select, from the plurality of learners, a second learner corresponding to each of the second site information and the second staining information; and
generate the model data based on the second learner and the second image data.

16. The first information processing device according to claim 1, wherein the circuitry is further configured to:
determine an existence of the model data corresponding to the second site information;
determine an accuracy of the model data based on the determination of the existence of the model data; and
generate new model data based on the accuracy of the model data.

17. An information processing method, comprising:
acquiring, by circuitry, first image data of an identification target, wherein the first image data includes first biological region of the identification target;
acquiring, by the circuitry, first site information of a plurality of pieces of site information, wherein
the first site information is associated with the first biological region, and
each piece of site information of the plurality of pieces of site information is associated with a respective identifier of a plurality of identifiers;
selecting, by the circuitry, an identifier corresponding to the acquired first site information, wherein the identifier is selected from the plurality of identifiers;
executing, by the circuitry, an identification process based on each of the selected identifier and the acquired first image data;
acquiring, by the circuitry, second image data of the identification target, wherein the second image data includes a second biological region of the identification target;
acquiring, by the circuitry, second site information of the plurality of pieces of site information, wherein
the second site information is associated with the second biological region,
each piece of site information of the plurality of pieces of site information is associated with a respective piece of model data of a plurality of pieces of model data, and
each piece of site information of the plurality of pieces of site information is associated with a respective learner of a plurality of learners;
selecting, by the circuitry, a learner corresponding to the acquired second site information, wherein the learner is selected from the plurality of learners; and
generating, by the circuitry, model data, of the plurality of pieces of model data, corresponding to the acquired second site information, wherein the model data is generated based on each of the selected learner and the acquired second image data.

18. An information processing system, comprising;
an information processing device that includes:
an image sensor configured to:
capture an image of an identification target; and
output first image data of the identification target based on the captured image; and
circuitry configured to:
acquire the first image data of the identification target, wherein the first image data includes a first biological region of the identification target;

acquire first site information of a plurality of pieces of site information, wherein
the first site information is associated with the first biological region, and
each piece of site information of the plurality of pieces of site information is associated with a respective identifier of a plurality of identifiers;
select, from the plurality of identifiers, an identifier corresponding to the acquired first site information;
execute an identification process based on each of the selected identifier and the acquired first image data;
acquire second image data of the identification target, wherein the second image data includes a second biological region of the identification target;
acquire second site information of the plurality of pieces of site information, wherein
the second site information is associated with the second biological region,
each piece of site information of the plurality of pieces of site information is associated with a respective piece of model data of a plurality of pieces of model data, and
each piece of site information of the plurality of pieces of site information is associated with a respective learner of a plurality of learners;
select, from the plurality of learners, a learner corresponding to the acquired second site information; and
generate model data, of the plurality of pieces of model data, corresponding to the acquired second site information, wherein the model data is generated based on each of the selected learner and the acquired second image data.

19. An information processing system, comprising:
a medical image imaging device configured to:
capture an image of an identification target; and
output first image data of the identification target based on the captured image; and a non-transitory computer-readable medium, having stored thereon, computer-executable instructions that, when executed by a computer, cause the computer to execute operations, the operations comprising:
acquiring the first image data of the identification target, wherein the first image data includes a first biological region of the identification target;
acquiring first site information of a plurality of pieces of site information, wherein
the first site information is associated with the first biological region, and
each piece of site information of the plurality of pieces of site information is associated with a respective identifier of a plurality of identifiers;
selecting, from the plurality of identifiers, an identifier corresponding to the acquired first site information;
executing an identification process based on each of the acquired first image data and the selected identifier;
acquiring second image data of the identification target, wherein the second image data includes a second biological region of the identification target;
acquiring second site information of the plurality of pieces of site information, wherein
the second site information is associated with the second biological region,
each piece of site information of the plurality of pieces of site information is associated with a respective piece of model data of a plurality of pieces of model data, and
each piece of site information of the plurality of pieces of site information is associated with a respective learner of a plurality of learners;
selecting, from the plurality of learners, a learner corresponding to the acquired second site information; and
generating model data, of the plurality of pieces of model data, corresponding to the acquired second site information, wherein the model data is generated based on each of the selected learner and the acquired second image data.

* * * * *